United States Patent [19]

Hisatsuka et al.

[11] E Re. 31,030

[45] Reissued Sep. 14, 1982

[54] PROCESS FOR THE PRODUCTION OF NOVEL POLYSACCHARIDE

[75] Inventors: Kenichi Hisatsuka; Saburo Ishiyama; Akira Inoue; Osamu Tsumura, all of Sodegaura; Mikio Sato, Ichihara, all of Japan

[73] Assignee: Idemitsu Kosan Company Limited, Tokyo, Japan

[21] Appl. No.: 184,017

[22] Filed: Sep. 4, 1980

Related U.S. Patent Documents

Reissue of:

[64] Patent No.: 4,153,508
Issued: May 8, 1979
Appl. No.: 839,900
Filed: Oct. 6, 1977

U.S. Applications:

[62] Division of Ser. No. 759,627, Jan. 17, 1977, Pat. No. 4,146,706.

[30] Foreign Application Priority Data

Jan. 19, 1976 [JP] Japan ..... 51/4051
Apr. 5, 1976 [JP] Japan ..... 51/37224

[51] Int. Cl.[3] ..... C12P 19/04; C12R 1/38

[52] U.S. Cl. ..... 435/101; 435/253; 435/830; 435/874

[58] Field of Search ..... 536/1, 4, 120; 435/101, 435/253, 830, 874

[56] References Cited

U.S. PATENT DOCUMENTS 3,649,454 3/1972 Isono et al. ..... 435/206
3,868,303 2/1975 Tsumura et al. ..... 435/206
3,960,832 6/1976 Kang et al. ..... 435/101
3,988,313 10/1976 Bouniot ..... 435/104

OTHER PUBLICATIONS

Buchman et al., *Bergey's Manual of Determinative Bacteriology,* 8th ed., Williams & Wilkins Co., (1974) Baltimore, pp. 224–227.

Dellweg, "Characterization of an Extracellular Polysaccharide from *Pseudomonas stutzeri*", *European J. Appl. Microbiol,* vol. 1 (1975), pp. 307–312.

Laine et al., "Gas-Liquid Chromatography of Carbohydrates", *Methods in Enzymology,* vol. XXVIII, part B, Academic Press, N.Y. (1972), pp. 159–166.

Palleroni et al., "Taxonomy of the Aerobic Pseudomonads: the Properties of the *Pseudomonas stutzeri* Group", *J. Gen. Microbiol.,* vol. 60 (1970) pp. 215–231.

Dellweg et al., "Characterization of an Extracellular Polysaccharide from *Pseudomonas stutzeri*", *Chem. Abstracts,* vol. 85, No. 11 (1976), p. 262, Abs. No. 74636p.

Hisatsuka et al., "Fermentative Production of Anthranilic Acid", *Chem. Abstracts,* vol. 85, No. 3 (1976) p. 507, Abs. No. 19060w.

Zevenhuizen, "Formation and Function of the Glycogen Like Polysaccharide of Arthrobacter", *Chem. Abstracts,* vol. 66, No. (1967) p. 55, Abs. No. 587b.

*Primary Examiner*—Thomas G. Wiseman

*Attorney, Agent, or Firm*—Frishauf, Holtz, Goodman & Woodward

[57] ABSTRACT

Polysaccharides forming gels are produced by cultivating [a] microorganism [such as Arthrobacter carbazolum] *strain* FERM 2574 *(ATCC-31258)* in a suitable medium.

1 Claim, 10 Drawing Figures

PROCESS FOR THE PRODUCTION OF NOVEL POLYSACCHARIDE

Matter enclosed in heavy brackets [ ] appears in the original patent but forms no part of this reissue specification; matter printed in italics indicates the additions made by reissue.

This is a division of application Ser. No. 759,627, filed Jan. 17, 1977 *now U.S. Pat. No. 4,146,706.*

FIELD OF THE INVENTION

The present invention relates to a novel polysaccharide and a process for the production thereof.

BACKGROUND OF THE INVENTION

Heretofore, various processes for producing a polysaccharide utilizing microorganism have been proposed. However, the greater part of these processes was concerned with a viscid polysaccharide and there have been very few reports concerning a process for the production of a polysaccharide forming a gel. In addition, the known polysaccharides characterized by gel-formation have been produced by utilizing sugars as the carbon source of a nutrient medium.

SUMMARY OF THE INVENTION

The present invention is based on the following observations:

(1) that microorganisms isolated from various types of soil have an ability for producing a polysaccharide forming a gel;

(2) that said microorganisms belong to the genus Arthrobacter;

(3) that the polysaccharide is accumulated in a culture broth when the microorganisms are cultivated with the nutrient medium;

(4) that the recovered polysaccharide has the property of forming a gel.

According to the present invention, a polysaccharide characterized by gel formation can be produced by cultivating a polysaccharide having gel forming property-producing microorganism [belonging to the genus Arthrobacter] in a medium containing assimilable carbon sources and nitrogen sources until said polysaccharide is substantially accumulated in the culture, and recovering the accumulated polysaccharide therefrom.

BRIEF EXPLANATION OF THE DRAWINGS

In FIG. 6, 1 and 2 show HA-1; 3 shows an internal standard (xylitol); 4 and 5 are mannose; 6 and 9 are glucose and 7 and 8 show HA-2, respectively.

EMBODIMENTS OF THE INVENTION

Figure 1:
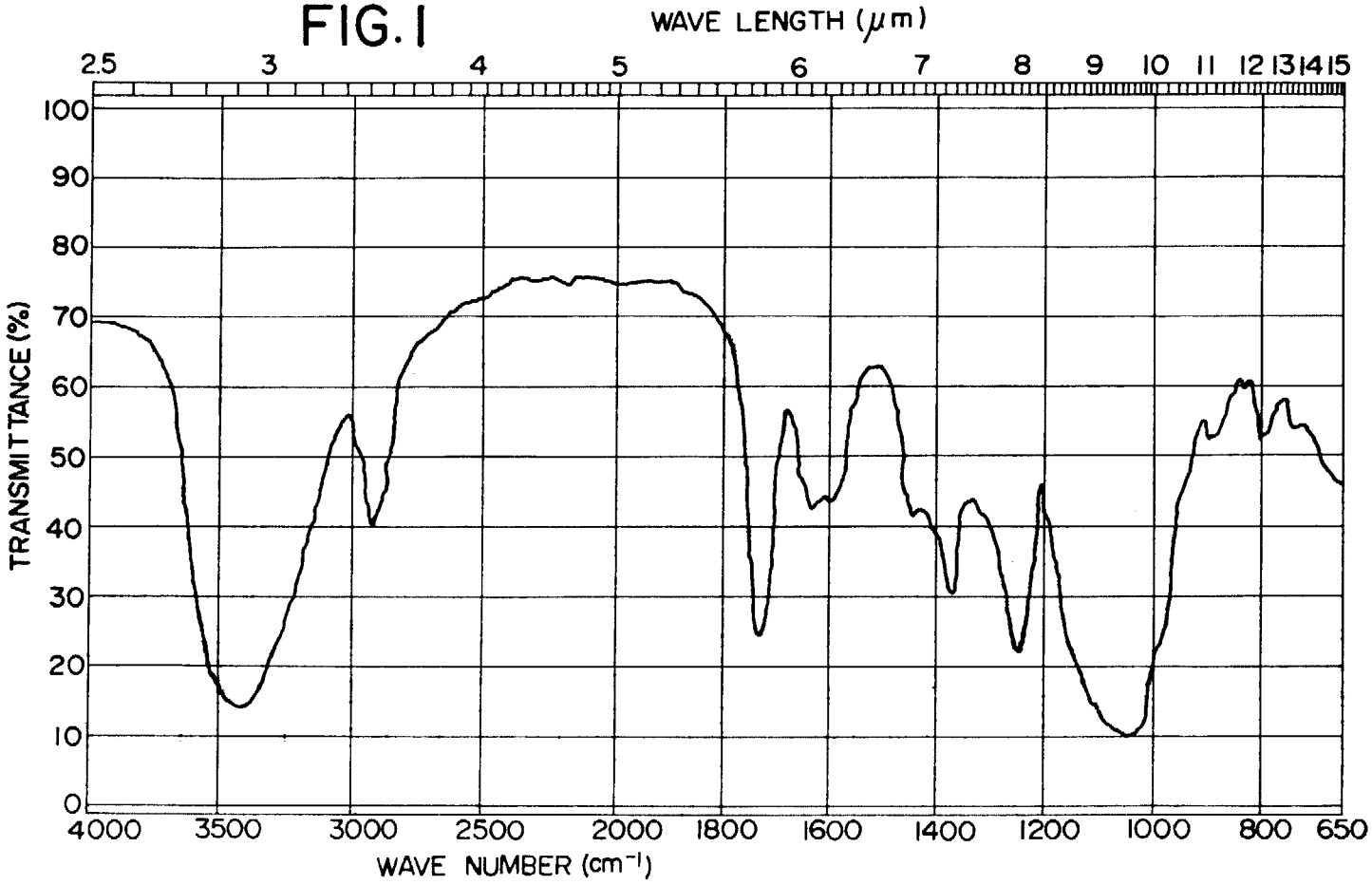
FIG. 1 shows IR absorption spectrum of the polysaccharide of this invention.

The microorganisms which can be employed in this invention [belong to the genus Arthrobacter, for example, Arthrobacter carbazolum, which] was isolated from soil [and named as above] by us. This strain was deposited in the Fermentation Research Institute, Agency of Industrial Science and Technology, Japan, and assigned the identification FERM-2574, and also deposited with the American Type culture Collection, Rockville, Md., U.S.A., and assigned the identification ATCC-31258. *It has been identified as Pseudomonas stutzeri.*

The microbial characteristics of said [Arthrobacter carbazolum] *microorganism* are as follows:

1. Microscopic Examination
size: $0.6–0.8 \times 1.2–2.7\mu$
figure: rod, [polymorphic]
gram stain: negative
spore: negative
[flagella: one to three peritrichous flagella]
2. Cultivation Examination with Medium
Bouillon agar plate culture: almost circular, rugose, undulate, semi-transparent, sticky;
Bouillon agar slant culture: good growth, rugose, spreading, sticky;
Bouillon broth culture: ring, pellicle, forming slight sticky sediment;
Bouillon agar stab culture: filiform, good growth in upper part;
Bouillon gelatine stab culture: growth only on surface, no liquefaction (cultivated for 40 days at 22° C.);
Growth in litmus milk: slightly alkaline, no coagulation;
Growth in potato-dextrose agar medium: moderate growth, no pigment;
3. Physiological Properties
Optimum pH for growth: 8–9
Optimum temperature for growth: 37° C.
pH range for growth: 5.5–9.5
[Temperature range for growth: 24°–43° C.]
Formation of indole: no
Formation of $H_2S$: yes
Formation of gas and organic acid from carbohydrate: no
Degradative ability of cellulose: no
Hydrolitic ability of starch: yes
Reduction of nitrate: yes
Availability of citric acid: yes
Methyl red test: negative
Voges-Proskauer test: negative
Formation of catalase: yes
Formation of ammonia: yes
Liquefaction of gelatin: no (cultivated for 50 days)
Availability of ammonium salt and nitrate: yes
Oxidase test: positive
Halophobicity against salt: no
Formation of urease: no
Growth in [both] aerobic [and anaerobic] conditions Availability of agar: no 4. Availability of Various Carbon Sources Glucose, [fructose,] maltose, glycerol, glycogen, [methanol,] *and* ethanol [and propanol] were utilized for growth.

Acid and gas formation tests were done according to the method of Hugh and Leifson (R. Hugh and E. Leifson: J. Bact., 66, 24 (1953)). As a result, acid and gas formation were not found in both aerobic and anaerobic conditions. Furthermore, in the case of using a fermentation tube with Ayer's and Barsiekov's medium (J. M. Pelczar: Manual of Microbiological Methods (McGraw-Hill) (1957), acid and gas formation were not found.

None of the arabinose, xylose, galactose, mannose, sucrose, lactose, trehalose, raffinose, salicin, mannitol, inositol or sorbitol was utilized.

[On the basis of microbiological characteristics abovedescribed, this strain was compared with those described in the 7th edition of Bergey's Manual of Determinative Bacteriology, and was considered to belong to the genus Arthrobacter from such points as polymorphic figure and soil bacteria which is in coccus-form in the later stage of the cultivation. As strains belonging to Arthrobacter which can utilize nitrates and ammonium salts as nitrogen sources and also possess hydrolitic ability of starch, Arthrobacter globiformis and Arthrobacter pascens are listed.] The strain isolated by us [is] *was* considered to resemble Arthrobacter pascens for the reason that it becomes remarkably sticky with the advance of growth. However, this strain is remarkably different from Arthrobacter pascens in view of action against gelatin and growth temperature, etc. The following differences between the two strains are listed in the following table.

| | *Arthrobacter pascens* | Strain isolated |
|---|---|---|
| Growth at 37° C. | no | yes |
| Liquefaction of gelatin | yes | no |
| Growth on the surface of a liquid medium | no | yes |
| Assimilation of carbazole | no | yes |

From these results, this strain was *earlier* identified as a new species belonging to Arthrobacter, and named Arthrobacter carbazolum to distinguish it from already-known strains. This [new] strain has been deposited as indicated above, *and now identified as Pseudomonas stutzeri.*

In the present invention, [all strains belonging to the genus Arthrobacter which possess an ability to produce a polysaccharide having gel forming property can also be used as well as] artificial or natural mutants of the strain described above *can also be used.*

In the case of cultivating this strain, such generally utilized substances as saccharides (for example, glucose, starch, etc.) can be used as carbon sources. In addition, acetic acid and such derivatives from petrochemistry as ethanol, glycerol, propanediol, butanediol, ethyleneglycol, etc., can also be used as carbon sources. As a nitrogen source, potassium nitrate, ammonium nitrate, ammonium sulfate, ammonium chloride, ammonium phosphate, polypeptone, carbazole, etc., can be used. As inorganic salts, dipotassium hydrogen phosphate or disodium hydrogen phosphate and potassium dihydrogen phosphate, etc., can be used, and as a source of a trace elemental metal, magnesium sulfate, ferrous sulfate, etc., can be used. A medium prepared by adding the above-described components into tap water was inoculated with the new strain, and cultivated in an aerobic condition by reciprocal shaking.

After completion of the cultivation, the polysaccharide accumulated in a culture broth can be harvested by various methods according to the purpose of use. For example, a water-soluble solvent such as methanol, ethanol, isopropanol, acetone, tetrahydrofurane, etc., is added in a high viscous broth to precipitate the polysaccharide with the cells, and after drying this precipitate can be used as a crude product.

When a solid material in the broth such as microbial cells is disadvantageous to the purpose of use, an appropriate amount of water is added before refining the broth, and the broth is heated. Subsequently, the polysaccharide is recovered from the solution obtained by centrifugation of the broth.

In refining, such routine methods for separation of the polysaccharide from impurities as condensation, precipitation with the above-described water-soluble solvent, precipitation with ammonium sulfate, washing, centrifugation, column chromatography, extraction with solvent, dialysis, etc., can be used singly or in combination. For example, after cultivation, an appropriate amount, preferably 3–10 times the amount based on the amount of the broth, of water is added into the broth, and the resultant mixture is heated to 45° to 65° C. The supernatant fluid is obtained by centrifugation of the broth. Subsequently, an aliphatic quarternary ammonium salt such as cetyl trimethyl ammonium bromide, etc., is added into this supernatant to precipitate the polysaccharide. The polysaccharide separated is washed with 85 to 95% methanol or ethanol saturated with sodium chloride or potassium chloride, etc. Thereafter, the polysaccharide is swelled by addition of water. After washing with acetone, etc., the polysaccharide is subjected to drying.

On the other hand, the polysaccharide can also be obtained by the addition of from 5 to 10 times the amount of water-soluble solvent such as acetone to precipitate the polysaccharide, or by spray-drying after desalting of the above supernatant by ultra-filtration or with an ion exchange resin such as Amberlite IR-120 B, Amberlite IRA-410, etc., and concentration. When a polysaccharide with higher purity is required, such procedures as deprotein using a mixture of chloroform and isoamyl alcohol (4:1) or dialysis can be applied in addition to the above-described procedures.

The polysaccharide thus obtained was studied on a physiochemical basis, and the results are summarized as shown below.

This polysaccharide does not correspond to the already-known compounds and therefore, was found to be a new compound.

(1) Elemental analysis: H: 5.50%; C: 38.02%; N: 0%.

Figure 2:
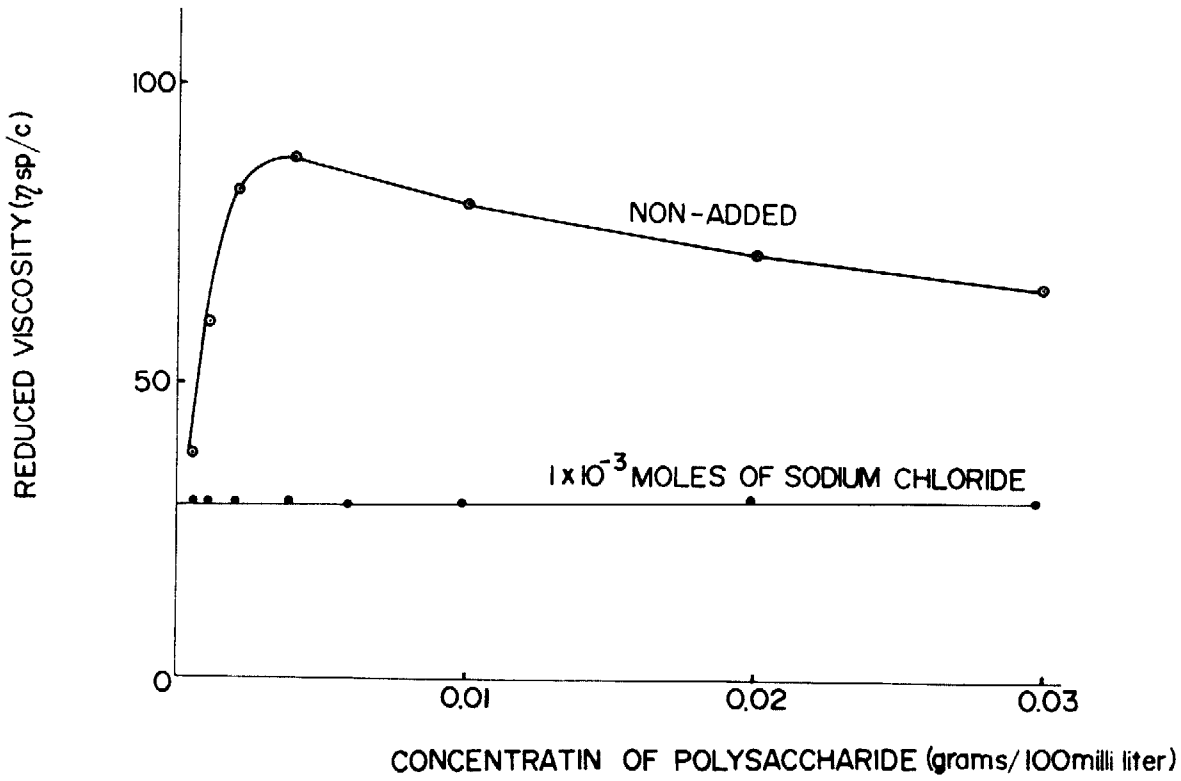
FIGS. 2, 3 and 4 are graphs of viscosity of the polysaccharide.

(2) Molecular weight: Molecular weight was measured by column chromatography using cephalose 2B (Pharmasia Co., Ltd., Sweden). The polysaccharide obtained was eluted in void-volume, so molecular weight was estimated as at least above 2,000,000. Furthermore, limiting viscosity was measured in the presence of sodium chloride ($1\times10^{-3}$ Mole), and as a result, $[\eta]$ was 29.0 dl/g at 25° C. FIG. 2). This value was applied to Staudinger's expression. From this result, the mean molecular weight was found to be about 8,000,000.

(3) Specific rotatory power: $[\alpha]_D^{23}=+20°-+35°$ (0.1% aqueous solution, l=0.1)

(4) Infrared absorption spectrum: IR absorption spectrum obtained with the method of KBr pellet is shown in FIG. 1.

(5) Solubility in solvent: The polysaccharide is not dissolved in organic solvents such as methanol, ethanol, acetone, ether, etc., and forms a gel in water. It is difficult to dissolve in water even at a low concentration (below 0.1%) and turns to a sticky solution when heated. A heated solution is colorless and transparent.

(6) Classification by acidity: The pH value of an aqueous solution of the polysaccharide solubilized as above-described was 3.0 to 3.5. Moreover, a precipitate was formed by adding cetyl trimethyl ammonium bromide. These results show that this polysaccharide is acidic.

(7) Color reaction: Blueish green by anthrone reaction.

(8) Color of polysaccharide: Colorless and transparent in dry condition and white in powder form.

(9) Melting point: No melting point; carbonization occurred when it was heated to about 235° C. It carbonized completely at about 280° C.

(10) Viscosity: From the result of measurement of specific viscosity with a Ubbelohde type viscometer, $\eta_{sp}$ was found to be 13 (C=0.1, 30° C.).

The relation between a reduced viscosity and a concentration of the polysaccharide, especially the effect of sodium chloride on a reduced viscosity was studied, and the result is shown in FIG. 2. The measurement of viscosity was carried out by using a Ubbelohde type viscometer at 25°±0.01° C.

Figure 3:
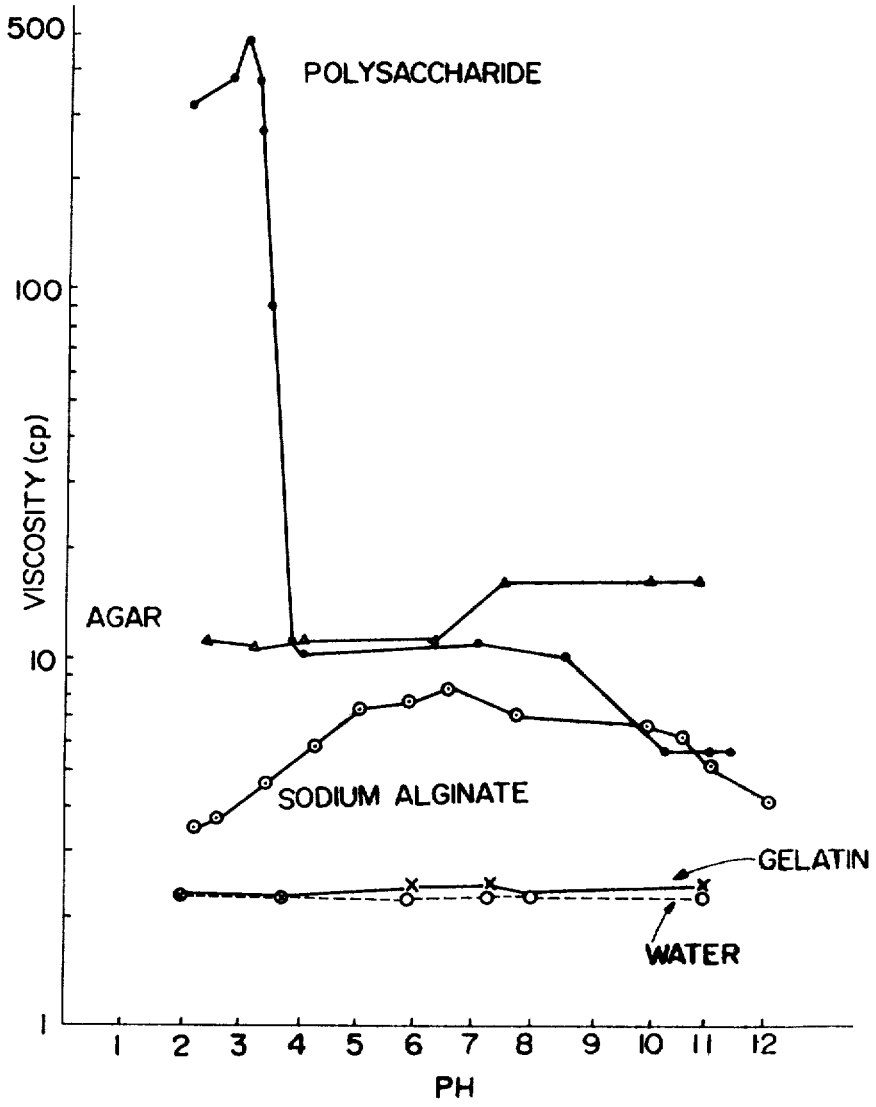
Figure 4:
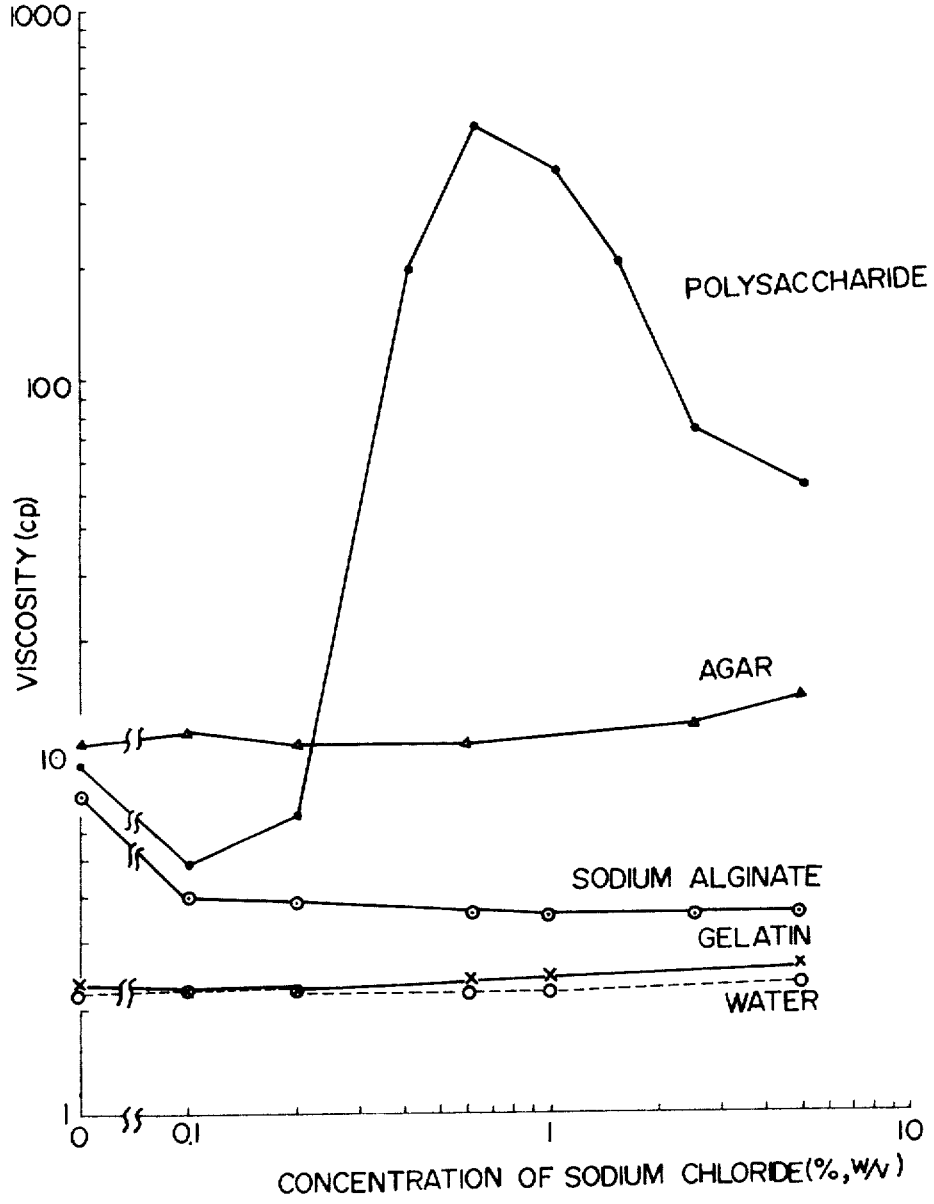

In addition, the effect of pH on viscosity was studied. From the results, it was found that viscosity was increased remarkably at about pH 3 and increased to 50 times compared with the value at pH 7 (FIG. 3). The measurement of viscosity was carried out with a B-type rotatory viscometer (Tokyo Keiki Co., Ltd.) at 30 r.p.m., a temperature of 25°±0.01° C. and 0.1% (w/v) of sample concentration. Agar, one of the samples, was dissolved by treating at 100° C. for 20 minutes. The other samples were treated at 60° C. for 10 minutes in order to solubilize. Adjustment of pH was done by adding dilute hydrochloric acid or dilute sodium hydroxide. The remarkable increase of viscosity was also observed by adding sodium chloride too (FIG. 4). Experimental conditions were the same as in the case of studying the effect of pH. These characteristics are specific to the polysaccharide of this invention.

(11) Physical characteristics of polysaccharide gel: The polysaccharide forms a gel containing water at the concentration of more than 0.5% of polysaccharide, and possesses the characteristic of solubility with heating and being coagulable with cooling, and furthermore, it forms a gel only by contacting with water at room temperature (as at about 21° C.).

Table 1 shows the results of physical properties of polysaccharide gels. Measurements were carried out as described below.

Water was added to a sample powder, and the resulting mixture was heated at 60° C. for 30 minutes with stirring. After cooling at room temperature (about 21° C.) for 1 hour, breaking strength (gel strength) and solidity of the gel were measured by using a curd meter (M-301 AR-type, Iio Denki Co., Ltd.).

TABLE 1

| | Effect of polysaccharide concentration on gel strength | | |
|---|---|---|---|
| Sample | Concentration (%) | Breaking (dyne/cm$^2$) | Solidity |
| agar | 0.5 | $2.25\times10^4$ | $9.90\times10^3$ |
| | 1.0 | $1.08\times10^5$ | $8.03\times10^4$ |
| | 2.0 | $5.56\times10^5$ | $3.19\times10^5$ |
| poly-saccharide | 0.5 | $<3.0\times10^3$ | $<1.0\times10^3$ |
| | 1.0 | $4.43\times10^4$ | $8.65\times10^3$ |
| | 2.0 | $5.78\times10^5$ | $3.28\times10^4$ |

The polysaccharide used as a sample was produced by using a fermentation medium containing ethanol and carbazole as main components, and washed with ethanol and acetone.

As shown in Table 1, the polysaccharide gels were soft and viscous in comparison with agar gels, and are assumed to have substantial elasticity from the fact that the gels are difficult to break. Actually, from the result of measurements of texture by using a rheolometer (produced by Iio Denki Co., Ltd.), it was found that the elasticity of the polysaccharide gels was as strong as that of polyurethane.

When a frozen gel was thawed, no phenomenon of leaving water was observed, and the gel was restored to the original state.

The polysaccharide obtained by the present invention has an ability to form a gel with water; moreover, it has a specific property to form a gel even with a solution containing a water-soluble organic solvent at high concentration. Table 2 shows the result of measurements of the effect of water content on gel formation. The measurements were carried out according to the following procedure. Polysaccharide powder (15 milligrams) was placed in a test-tube, and various amounts of organic solvent (1 milliliter) were added. After heating at 60° C. for 30 minutes, a solution was cooled and then yes (+) or no (−) on gel formation was checked. Sign ± designates jelly form.

TABLE 2

| | Minimum amount of water required for geling of organic solvent | | | |
|---|---|---|---|---|
| | Solvent | | | |
| Water | Methanol | Ethanol | Isopropanol | Acetone |
| 50% (v/v) | + | + | + | + |
| 40 | + | + | + | + |
| 25 | + | + | + | + |
| 20 | + | + | ± | − |

TABLE 2-continued

| Water | Minimum amount of water required for geling of organic solvent: Solvent: Methanol | Ethanol | Isopropanol | Acetone |
|---|---|---|---|---|
| 15 | + | + | – | – |
| 10 | ± | – | – | – |
| 0 | – | – | – | – |

Figure 5:
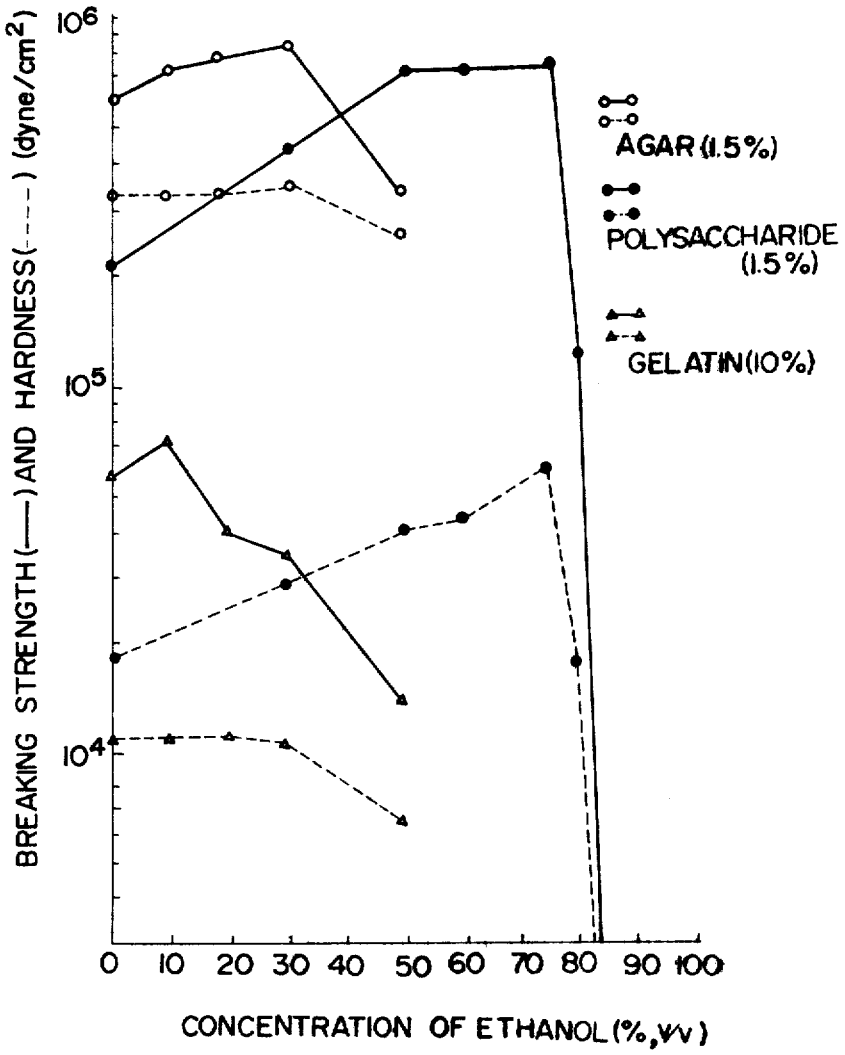
FIG. 5 shows the effect of ethanol concentration on the gel strength of the polysaccharide.

As shown in Table 2, gel formation did not occur in the absence of water, but a gel was formed in the presence of a relatively small amount of water. Next, the effect of ethanol concentration on breaking strength (gel strength) was studied. The results are shown in FIG. 5, indicating the maximum strength at 50–75% of ethanol concentration. In a reference test using agar or gelatin, gel formation occurred up to a concentration of 50%, but these samples were precipitated at a concentration of more than 50%. On the other hand, the polysaccharide obtained by this invention formed a gel with 85% of ethanol. Conditions for forming a gel are described in the following. Polysaccharide powder was mixed with the solution containing various amounts of ethanol, and polysaccharide gels were prepared by heat treatment at 60° C. for 30 minutes. Agar gels were prepared as follows. Powder was solubilized by heat treatment at 100° C. for 10 minutes, and ethanol was added to the solution after cooling at 60° C. Gelatin gels were prepared in the same manner as agar, except the heat treatment was done at 60° C. for 20 minutes. Increase of breaking strength was observed by adding sodium chloride (0.1% to 10% concentration).

Further, stress relaxation of a polysaccharide gel was compared with that of agar gel. The measurement was carried out by using a rheolometer (RMT-1300, Iio Denki Co., Ltd.) at a sample concentration of 2.0% (w/v) adjusting with water as a solvent.

TABLE 3

| Property | | Stress relaxation: Polysaccharide gel | Agar gel |
|---|---|---|---|
| Modulus of elacticity | Y1 | $1.01 \times 10^5$ dyne/cm$^2$ | $2.27 \times 10^5$ dyne/cm$^2$ |
| | Y2 | $3.26 \times 10^4$ | $1.53 \times 10^5$ |
| | Y3 | $1.83 \times 10^4$ | $9.88 \times 10^4$ |
| Coefficient of viscosity | $\eta 1$ | $\infty$ dyne.sec./cm$^2$ | $\infty$ dyne.sec./cm$^2$ |
| | $\eta 2$ | $5.38 \times 10^6$ | $6.74 \times 10^7$ |
| | $\eta 3$ | $3.75 \times 10^5$ | $1.13 \times 10^7$ |
| Relaxation time | $\tau 1$ | $\infty$ sec. | $\infty$ sec. |
| | $\tau 2$ | 165.0 | 440.0 |
| | $\tau 3$ | 20.5 | 115.0 |

Figure 6:
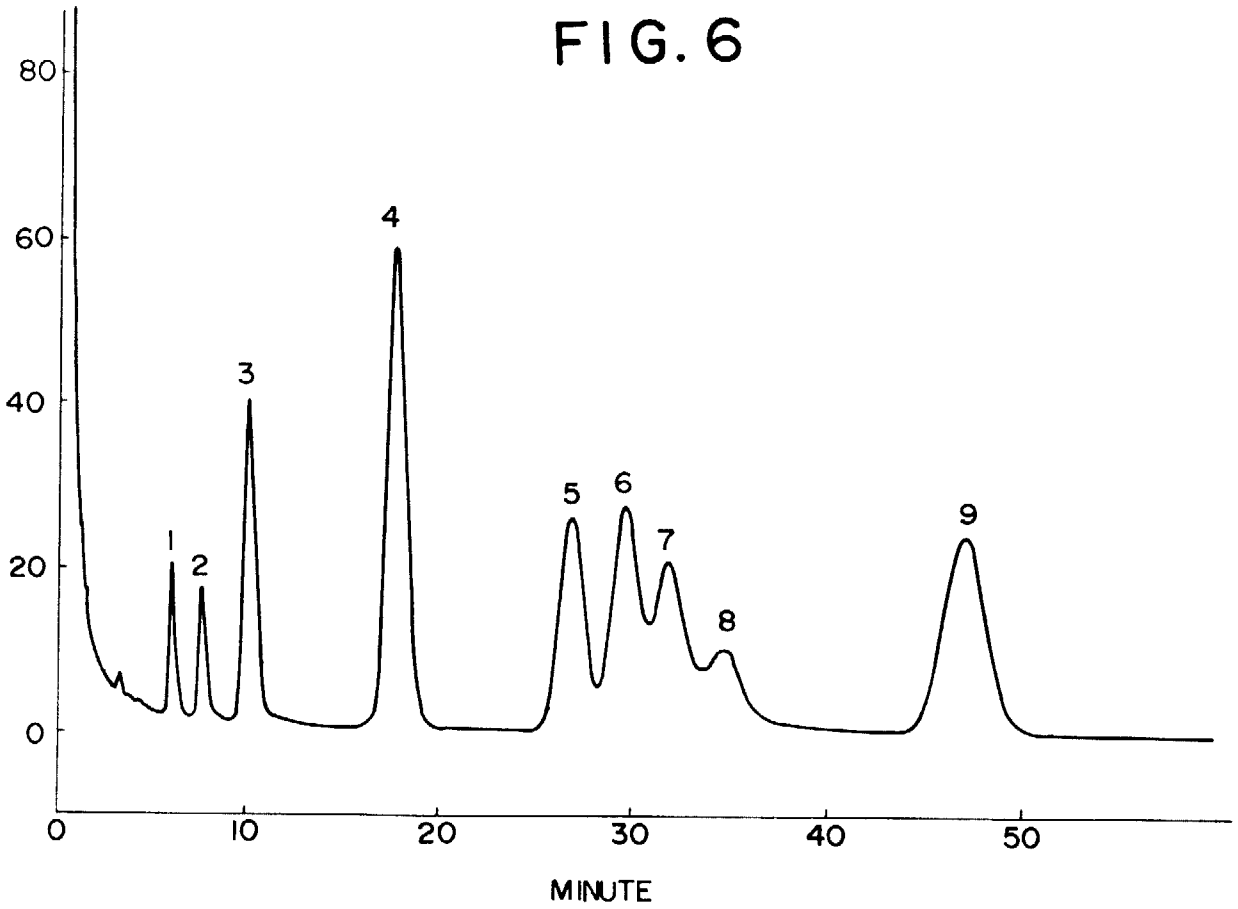
FIG. 6 shows a gas chromatogram of a trimethylsilyl derivative of a hydrolysate of the polysaccharide (condition of measurement: column 5% Silicone OV-17 on Chromosorb W, 2 meter of glass, temperature of 150° C.).

(12) Components of polysaccharide:

Purified polysaccharide was hydrolized by 1 N-sulfuric acid at 100° C. for 6 hours, and the reaction mixture was neutralized by adding barium carbonate. After centrifugation, the resulting supernatant was analyzed by paper chromatography, thin-layer chromatography and gas chromatography of a trimethylsilyl derivative. Table 4 shows the $R_f$ value of the decomposed polysaccharide in paper chromatography, and FIG. 6 shows a gas chromatogram of the trimethylsilyl derivative. From these results, it was found that the polysaccharide of this invention comprises glucose, mannose, unknown neutral sugar and unknown acidic sugar.

TABLE 4

| Constituent sugar | Solvent for development | $R_f$ value | Reagent for detecting |
|---|---|---|---|
| glucose | | 0.13 | p-anisidine, silver nitrate |
| mannose | | 0.19 | p-anisidine, silver nitrate |
| unknown neutral sugar | butanol:acetic acid:water = 4:1:1 | 0.46 | silver nitrate |
| unknown acidic sugar | | 0.55 | p-anisidine, bromocresol green |
| glucose | | 0.60 | p-anisidine, silver nitrate |
| mannose | isopropanol:pyridine:water:acetic acid = 8:8:4:1 | 0.65 | p-anisidine, silver nitrate |
| unknown neutral sugar | | 0.81 | silver nitrate |
| unknown acidic sugar | | 0.75 | p-anisidine, bromocresol green |

Structural elucidation of unknown neutral sugar (designated as HA-1 hereafter) and unknown acidic sugar (designated as HA-2 hereafter) was carried out as described below.

(1) Identification of HA-1

Hydrolyzed product of the polysaccharide was applied to a charcoal column chromatography, and eluted with water, 10% of ethanol and ethanol in this order. Glucose and mannose were found in the water-eluted fraction, and HA-1 and HA-2 were found in 10% ethanol-eluted and ethanol-eluted fractions, respectively.

Figure 7:
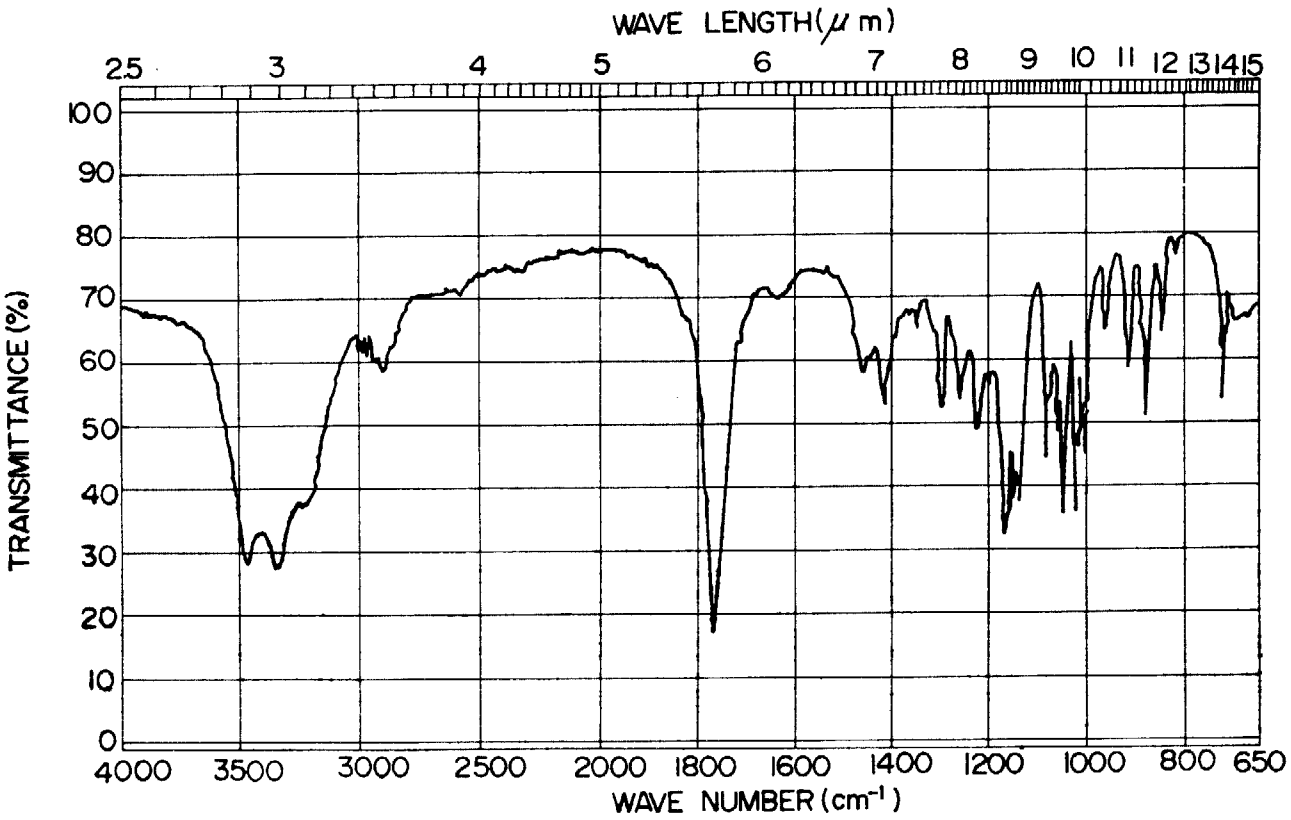
FIG. 7 is the IR absorption spectrum of crystals of the oxidation product of HA-1.

The 10% ethanol-eluted fraction was concentrated to dryness and was purified by ion exchange column chromatography (Dowex 1×8, borate type), and HA-1 was isolated from the resulting 0.015 mole of potassium borate eluted fraction. HA-1 was unstable and difficult to crystallize, so an oxidation reaction with bromine was made. That is, 40 milligrams of HA-1 was dissolved in 2 milliliters of bromine water in the presence of 240 milligrams of strontium carbonate, and reacted at 30° C. overnight. After the reaction, the reaction mixture was filtered and bromine in the filtrate was removed under a reduced pressure. Subsequently, the filtrate was treated with silver carbonate. After removal of the resulting precipitate, the reaction product was applied to ion exchange column chromatography (Dowex 1×8, acetate-type) to obtain crude crystals from 2 moles of an acetic acid eluted fraction. The crude crystals obtained were recrystallized in acetone-ethyl acetate to form 20 milligrams of colorless needle crystals. The crystals were analyzed by several physical methods, and results are shown below. FIG. 7 shows the IR absorption spectrum of the crystals.

(a) Melting point: 139°–142° C.

| | (b) Elemental Analysis: Calculated ($C_6H_{10}O_5$) | Found |
|---|---|---|
| C | 44.44% | 44.59% |
| H | 6.22% | 6.14% |

-continued

| (b) Elemental Analysis: | | |
|---|---|---|
| | Calculated ($C_6H_{10}O_5$) | Found |
| O | 49.34% | 49.31% |

(c) Absorption range in IR absorption spectrum (KBr tablet method): 3200–3450 $cm^{-1}$(OH), 2850–3000, 1460, 1360, 1342 $cm^{-1}$(CH, $CH_2$, $CH_3$), 1770, 1755 $cm^{-1}$(C=O in lactone), 1405 $cm^{-1}$(OH), 1290, 1250, 1220, 1160, 1135, 1078, 1043, 1015 $cm^{-1}$(C—OH, COO, CO in C—O—C), 955 $cm^{-1}$, 906 $cm^{-1}$, 843 $cm^{-1}$, 768 $cm^{-1}$.

(d) Absorption range in NMR spectrum $$\overset{O}{\overset{\|}{C}}$$

(solvent: $CD_3CCD_3$)

8.67 $\tau$(d, J=6 Hz, $CH_3$ of $C_5$ position), 6.39 $\tau$(d, J=5.5 HZ, $CH_2OH$ of $C_3$ position), 5.97 $\tau$(s, OH of $C_3$ position), 5.65 $\tau$(t, J=5.5 Hz, $CH_2OH$ of $C_3$ position), 5.41 $\tau$(d, J=8 Hz, CH of $C_2$ position), 5.38 $\tau$(q, J=6 Hz, CH of $C_4$ position), 5.00 $\tau$(d, J=8 Hz, OH of $C_2$ position).

An absorption range of HA-1 which is a compound before oxidation with bromine, in NMR spectrum (solvent: $D_2O$) was as follows: 8.76 $\tau$(d, J=6.5 Hz, $CH_3$ of $C_5$ position), 6.40 $\tau$(s, $CH_2OH$ of $C_3$ position), 5.93 $\tau$(d, J=5 Hz, CH of $C_2$ position), 5.61 $\tau$(q, J=6.5 Hz, CH of $C_4$ position), 4.70 $\tau$(d, J=5 Hz, CH of $C_1$ position).

Based on the above-described analysis, the product derived from oxidation of HA-1 was identified as dihydrostreptosonic acid monolactone, and HA-1 was identified as dihydrosreptose. Chemical structure of dihydrostreptose is shown below.

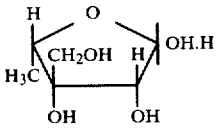

(2) Structural analysis of HA-2

(A) Estimation of structure

After concentration of the ethanol eluted fraction in charcoal column chromatography, the concentrates were treated by ion exchange column chromatography (Dowex 1×8, acetate type). From the 5 moles of the resulting acetic acid eluted fraction, a mixture of acidic-type and lactone-type HA-2 was obtained. First in order to isolate the lactone-type, silica gel column chromatography was carried out, and crude crystals of lactone-type were obtained from the eluted fraction (benzene:ethyl acetate=2:1). The crude crystals were recrystallized in ethyl acetate-hexane to form 100 milligrams of colorless needle crystals.

Figure 8:
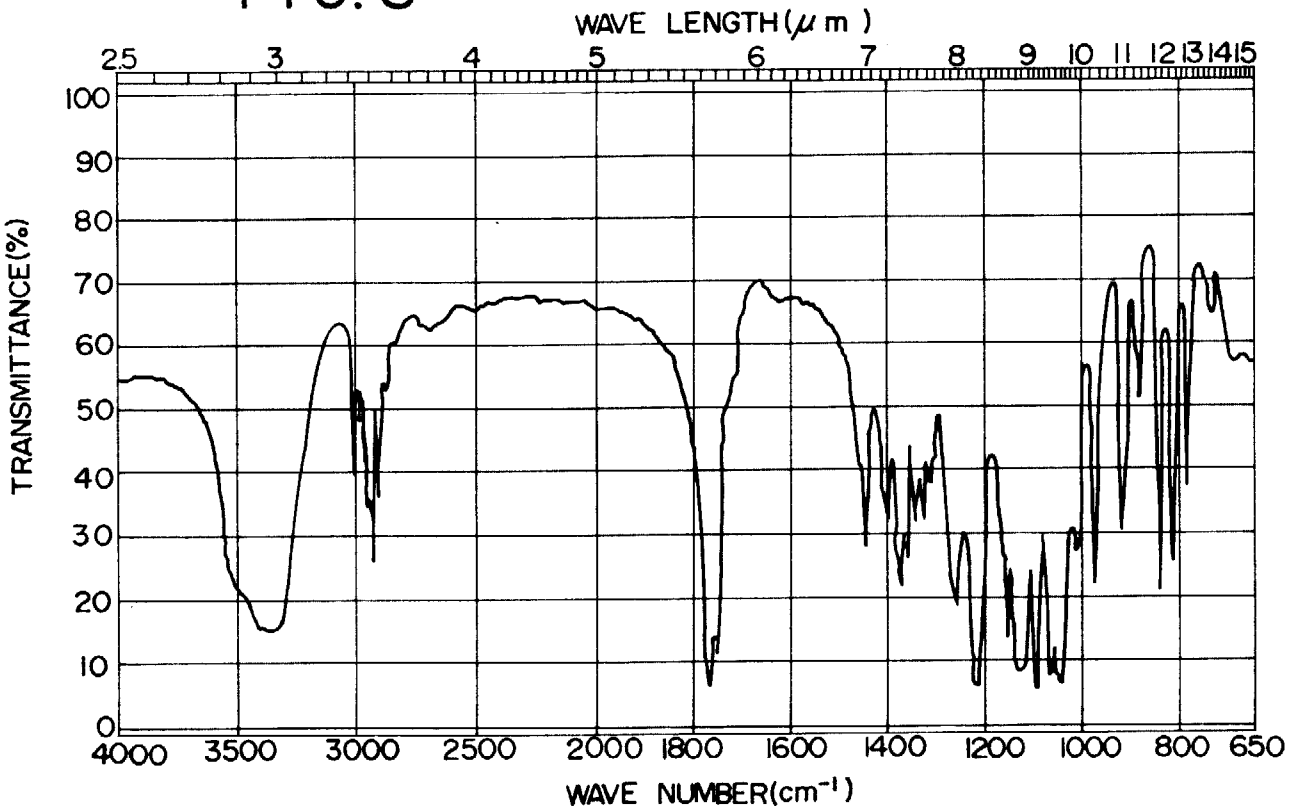
FIG. 8 is the IR absorption spectrum of crystals of the lactone-type of HA-2.
Figure 9:
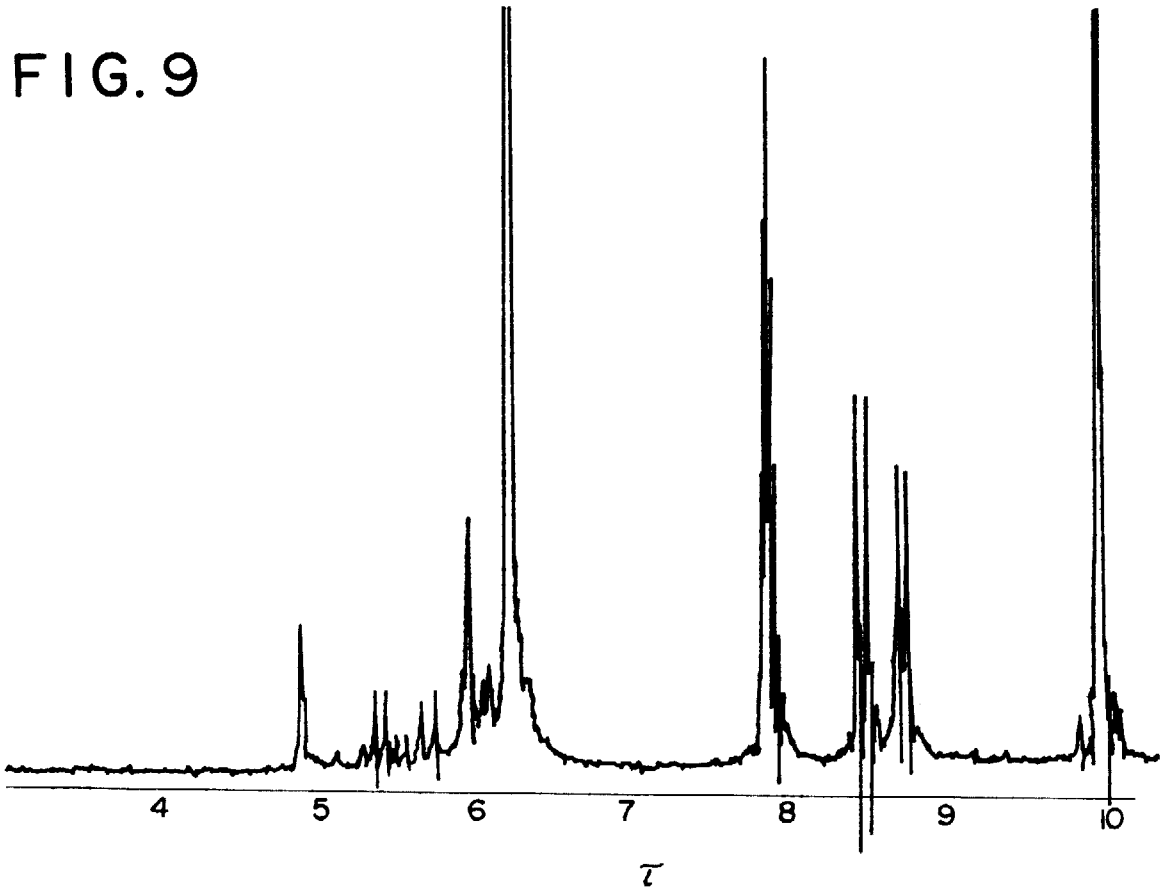
FIG. 9 is the NMR spectrum of crystals of the lactone-type of HA-2.

Results of analysis of the crystals of lactone-type of HA-2 were as follows. FIG. 8 and FIG. 9 show the IR absorption spectrum and NMR spectrum of the crystals, respectively.

(1) Melting point: 136°–137° C.

| (2) Elemental Analysis: | | |
|---|---|---|
| | Calculated ($C_9H_{14}O_6$) | Found |
| C | 49.54% | 49.68% |
| H | 6.47% | 6.34% |
| O | 44.00% | 43.87%. |

(3) Absorption range in IR absorption spectrum (KBr tablet method): 3350 $cm^{-1}$(OH), 2850–3000, 1440, 1360–1370, 1320–1340 $cm^{-1}$(CH, $CH_3$), 1730–1760 $cm^{-1}$(C=O in lactone), 1258, 1215, 1085, 1065, 1040 $cm^{-1}$(C—OH, COO, C—O in C—O—C), 975 $cm^{-1}$(terminal $CH_3$), 918, 780 $cm^{-1}$(pyranose ring), 885 $cm^{-1}$(CH except for anomer CH), 840 $cm^{-1}$(anomer CH), 810 $cm^{-1}$.

(4)

$$\overset{O}{\overset{\|}{C}}$$

NMR spectrum (solvent: $CD_3CCD_3$ + $D_2O$)

8.74 $\tau$ (d, J = 6 Hz, 3H $-\overset{O}{\overset{|}{C}}H-CH_3$);

8.48 $\tau$ (d, J = 7 Hz, 3H $-\overset{O}{\overset{|}{C}}H-CH_3$);

5.96–6.20 $\tau$ (m, 3H, unknown);

5.68 $\tau$ (d—d, J = 10 Hz, 1H $-\overset{|}{C}H-\overset{O}{\overset{|}{C}}H-\overset{|}{C}H-$);

5.41 $\tau$ (q, J = 7 Hz, 1H $-\overset{O}{\overset{|}{C}}H-CH_3$);

4.90 $\tau$ (s, 1H, anomer H).

Based on the results above-described, the crystals of lactone-type HA-2 were elucidated as a compound in which 6-deoxy hexose and lactic acid form an ether linkage, and a carboxyl group of lactic acid forms a lactone linkage with a hydroxyl group of 6-deoxy hexose. In order to elucidate the more detailed structure, various kinds of derivatives of HA-2 were prepared, and then these derivatives were analyzed by NMR spectrometry. The methods of preparation of derivatives are described below, and the results of NMR spectrometry are shown in Table 5. $D_6$-acetone was used as solvent in measuring the NMR spectra.

(a) Synthesis of acetyl derivative of HA-2 (lactone-type) (III)

Crystals of lactone-type HA-2 (34 milligrams) were dissolved in 1 milliliter of a mixture solution (acetic anhydride:pyridine=2:1), and reacted overnight at room temperature. After removal of solvent, silica gel column chromatography was carried out. From the resulting eluted fraction (benzene:ethyl acetate=9:1), 34 milligrams of the derivative (III) were isolated.

(b) Synthesis of methyl glycoside derivative of HA-2 (lactone-type) (IV)

A mixture of acidic-type and lactone-type HA-2 (47 milligrams) was dissolved in 10 milliliters of a hydrochloride-methanol solution (2.5 percent solution), and reaction was carried out for 6 hours under boiling reflux. After the removal of solvent, silica gel column chromatography was carried out. From the resulting eluted fraction (benzene:ethyl acetate=5:1), 32 milligrams of the derivative (IV) were isolated.

(c) Synthesis of methyl ester derivative of HA-2 (acidic-type) (V)

A mixture of acidic-type and lactone-type HA-2 (110 milligrams) was dissolved in methanol, and mixed with an ether solution of diazomethane. After reaction at room temperature for a night, solvent was removed, and then subjected to silica gel column chromatography. From the resulting eluted fraction (benzene:ethyl acetate=7:3), 66 milligrams of the derivative (V) were isolated.

(d) Synthesis of perfect acetyl derivative of methyl ester of HA-2 (acidic-type) (VI)

Twenty four milligrams of the compound (V) obtained by the above-described reaction (c) were dissolved in 1 milliliter of a mixture solution (acetic anhydride:pyridine=2:1), and reaction was carried out overnight at room temperature. After the removal of solvent, silica gel column chromatography was carried out, and 20 milligrams of compound (VI) were isolated from the eluted fraction (benzene:ethyl acetate=9:1).

(e) Synthesis of partial acetyl derivative of methyl ester of HA-2 (acidic-type) (VII)

Twenty three milligrams of the compound (III) obtained by the reaction (a) were mixed with a small amount of water to open the lactone ring, and an ether solution of diazomethane was added, followed by a reaction at room temperature overnight. After the removal of solvent, silica gel column chromatography was carried out, and 17 milligrams of the compound (VII) were isolated from the resulting eluted fraction (benzene:ethyl acetate=7:1).

From the results of analysis shown in Table 5, structures of HA-2 (acidic-type) (I), HA-2 (lactone-type) (II) and various kinds of derivatives were estimated as follows:

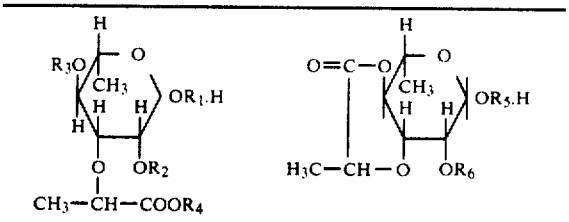

| | |
|---|---|
| HA-2 (acidic-type) (I) | $R_1 = R_2 = R_3 = R_4 = H$ |
| HA-2 (lactone-type) (II) | $R_5 = R_6 = H$ |
| Derivative (III) | $R_5 = R_6 = CH_3CO$ |
| Derivative (IV) | $R_5 = CH_3$, $R_6 = H$ |
| Derivative (V) | $R_1 = R_2 = R_3 = H$, $R_4 = CH_3$ |
| Derivative (VI) | $R_1 = R_2 = R_3 = CH_3CO$, $R_4 = CH_3$ |
| Derivative (VII) | $R_1 = R_2 = CH_3CO$, $R_3 = H$, $R_4 = CH_3$ |

TABLE 5

NMR spectra of various derivatives of HA-2 (solvent: $D_6$-acetone)

| Derivative / Proton | II | III | IV | V | VI | VII |
|---|---|---|---|---|---|---|
| CH of $C_1$ position | 4.90 $\tau$ | d 4.02 $\tau$, $J_{1-2}$ 1.95Hz | 5.36 $\tau$ | d 4.96 $\tau$, $J_{1-2}$ 2Hz | d 4.04 $\tau$, $J_{1-2}$ 2Hz | d 4.08 $\tau$, $J_{1-2}$ 2Hz |
| CH of $C_2$ position | 6.02 $\tau$ | d-d 4.72 $\tau$, $J_{1-2}$, $J_{2-3}$ 1.95Hz 3Hz | 6.00 $\tau$ | d-d 6.07 $\tau$, $J_{1-2}$, $J_{2-3}$ 2Hz 2Hz | d-d 4.68 $\tau$, $J_{1-2}$, $J_{2-3}$ 2Hz 3Hz | d-d 4.72 $\tau$, |
| CH of $C_3$ position | 5.96-6.20 $\tau$ | d-d 5.78 $\tau$, $J_{2-3}$, $J_{3-4}$ 3Hz 9-10Hz | d 6.17 $\tau$, $J_{3-4}$ 9Hz | 6.2-6.4 $\tau$ | d-d 6.12 $\tau$, $J_{2-3}$, $J_{3-4}$ 3Hz 9Hz | 6.2-6.4 $\tau$ |
| CH of $C_4$ position | d-d 5.68 $\tau$, $J_{3-4}$, $J_{4-5}$ 10Hz 10Hz | d 5.74 $\tau$, $J_{3-4}$ 9-10Hz | d-d 5.70 $\tau$, $J_{3-4}$, $J_{4-5}$ 9Hz 9Hz | d-d 6.54 $\tau$, $J_{3-4}$, $J_{4-5}$ 9Hz 10Hz | d-d 5.08 $\tau$, $J_{3-4}$, $J_{4-5}$ 9Hz 9Hz | d-d 6.55 $\tau$, |
| CH of $C_5$ position | 5.96 $\tau$ | q 5.96 $\tau$, $J_{5-6}$ 6Hz | d-q 6.28 $\tau$, $J_{4-5}$, $J_{5-6}$ 9Hz 6Hz | 6.24 $\tau$ | d-q 6.12 $\tau$, $J_{4-5}$, $J_{5-6}$ 9Hz 8Hz | 6.2-6.4 $\tau$ |
| CH of $C_6$ position | d 8.74 $\tau$, $J_{5-6}$ 6Hz | d 8.74 $\tau$, $J_{5-6}$ 6Hz | d 8.74 $\tau$, $J_{5-6}$ 6Hz | d 8.84 $\tau$, $J_{5-6}$ 6Hz | d 8.88 $\tau$, $J_{5-6}$ 8Hz | d 8.78 $\tau$, $J_{5-6}$ 6Hz |
| CH of lactic acid moiety | q 5.41 $\tau$, 7Hz | q 5.42 $\tau$, 6Hz | q 5.44 $\tau$, 7Hz | q 5.70 $\tau$ 7Hz | q 5.84 $\tau$, 7Hz | q 5.72 $\tau$, 6Hz |
| $CH_3$ of lactic acid moiety | d 8.48 $\tau$, 7Hz | d 8.54 $\tau$, 6Hz | d 8.53 $\tau$, 7Hz | d 8.68 $\tau$, 7Hz | d 8.82 $\tau$, 7Hz | d 8.72 $\tau$, 6Hz |

(B) Identification of constituent sugar in HA-2

Confirmation of the constituent sugar in HA-2 was done by the following analytical method.

Thirty milligrams of derivative (V) obtained by the above-described reaction (c) were dissolved in 1 milliliter of water, and 10 milligrams of sodium borohydride were added. After 3 hours of reaction at room temperature, an excess of cation exchange resin (Amberlite IR-120 B, H type) was added to the reaction mixture in order to decompose the unreacted sodium borohydride. Supernatant obtained by filtration was evaporated at a reduced pressure, and methanol was added. By repeating this evaporation, the remaining boric acid was removed.

As a result, 20 milligrams of reduction product (VIII) were obtained. A part of compound (VIII) (10 milligrams) was dissolved in 20 milliliters of anhydrous methylene chloride, and then the reaction atmosphere was replaced by argon gas. After cooling to −78° C., 4 milliliters of boron trichloride were added, and reacted overnight. After the reaction, methanol was added to the reaction mixture to decompose boron trichloride, and solvent was removed. Methanol was added to the residue, and evaporated at a reduced pressure. This evaporation was repeated. The residue was dissolved in water and deionized with an ion exchange resin to concentrate and dry. By this procedure, 7 milligrams of sugar alcohol (IX) derived from the constituent sugar of HA-2 were isolated. From the result of the analysis with gas chromatography of a trimethylsilyl or acetyl derivative of the sugar alcohol (IX), it was found that retention time of these derivatives was coincident with that of various derivatives of L-rhamnitol prepared by the reduction of L-rhamnose. In addition, IR absorption spectrum and NMR spectrum of the acetyl derivative (X) also coincided with that of the acetyl derivative of L-rhamnitol. Accordingly, the constituent sugar of HA-2 was identifed as L-rhamnose. Structures of various derivatives used in this identification process are as follows:

| | |
|---|---|
| $CH_2OR_1$ | Reduction product (VIII) |
| $HCOR_2$ | $R_1 = R_2 = R_4 = R_5 = H$ |
| $HCOR_3$ | $R_3 = CH_3CHCH_2OH$ |
| $R_4OCH$ | Sugar alcohol (IX) |
| $R_5OCH$ | $R_1 = R_2 = R_3 = R_4 = R_5 = H$ |
| $CH_3$ | Acetyl derivative of sugar alcohol (X) $R_1 = R_2 = R_3 = R_4 = R_5 = CH_3CO$ |

(C) Confirmation of the site of ether linkage between L-rhamnose and lactic acid Ten milligrams of the reduction product (VIII) were dissolved in 1 milliliter of a mixture solution of acetic anhydride and pyridine (2:1), and reaction was carried out overnight at room temperature. After the removal of solvent, the reaction product was purified by silica gel column chromatography, and 10 milligrams of acetyl derivative (XI) were isolated.

This compound (XI) was applied to gas mass-spectroscopy, and fragments of [M-145 and M-159] *m/l-145 and m/l-159* were observed. From this result, it was confirmed that lactic acid is joined by an ether linkage at the $C_3$ position of L-rhamnose. Assumptions in regard to the fragments are discussed below.

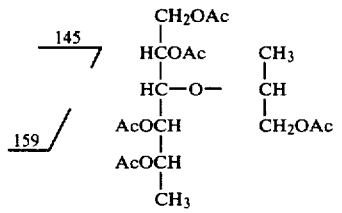

Derivative (XI)

Ac: $CH_3CO$

Based on the above-described analytical results, the structure of HA-2 was concluded to be 3-O-(1'-carboxy ethyl)-L-rhamnose, a new acidic sugar. This is shown below:

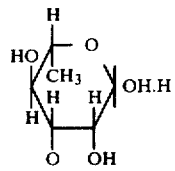

$CH_3—CH—COOH$
Acidic type

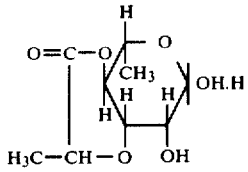

Lactose type

From these results, it was found that the constituent sugars of the polysaccharide obtained by the present invention are glucose, mannose, dihydrostreptose and 3-O-(1'-carboxy ethyl)-L-rhamnose, and the molar ratio of these constituent sugars in the polysaccharide was found to be 10:10:1-3:3-8 depending on the result of gas chromatography of the trimethylsilyl derivatives.

In addition, this polysaccharide contains an O-acetyl group, and its content was found to be 8-14 weight percent calculated as acetic acid from the result of gas chromatographic analysis of acetic acid, which was formed in the incubation of the polysaccharide with 1 N-sodium hydroxide for 1 hour at 40° C.

The polysaccharide obtained by the present invention not only possesses viscidity, but also forms a gel having a different property from that of agar. In the gel formation, the treatment of heating or cooling is not always necessary, that is, a gel can be formed only by contacting the polysaccharide with water at room temperature. Moreover, this polysaccharide has the property of forming a gel at a low concentration, and addition of a cross-linking agent and adjustment of pH are not needed to form a gel. In addition, this polysaccharide can form a gel immediately at a low temperature even in the presence of an organic solvent such as alcohols, organic acids and sugars, or water-soluble compounds such as salts. In this case, gel forming ability of this polysaccharide is not affected even if the water-soluble compound is present in a saturated concentration.

In the formed gel, the phenomenon of water release when the frozen gel is thawed is not observed. In addition, the gel has excellent water-retaining ability.

Figure 10:
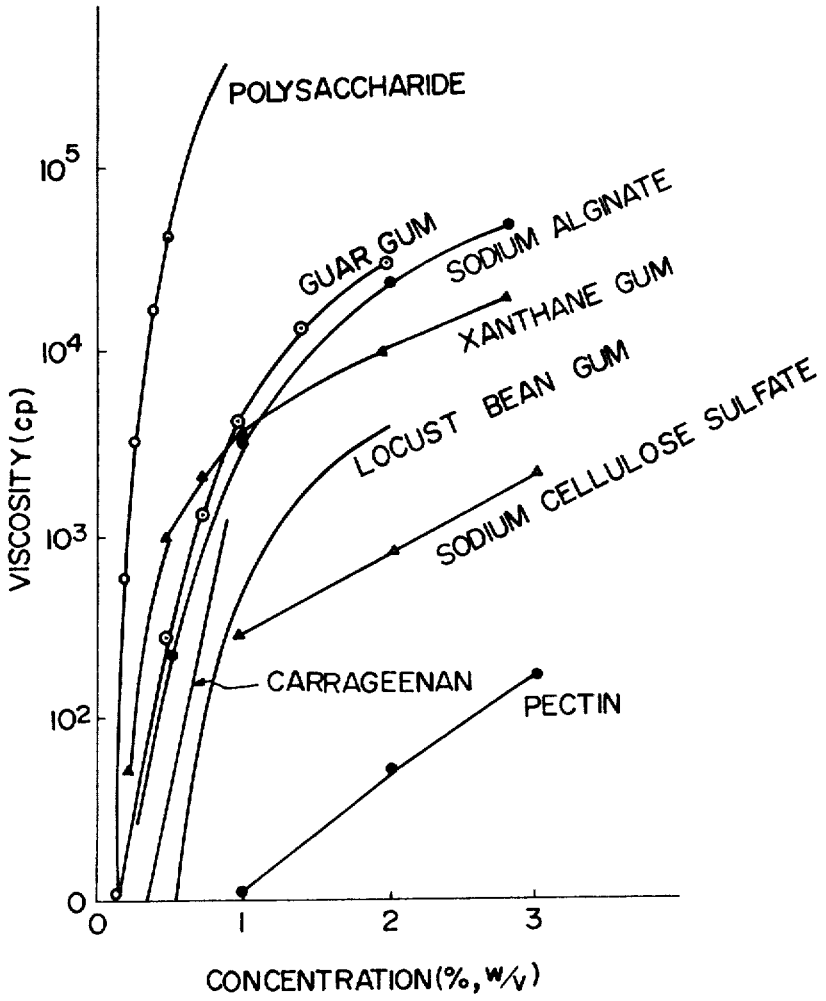
FIG. 10 shows graphs of viscosity of the polysaccharide solution, etc. (condition: B type rotary viscometer, 25° C., 30 r.p.m.).

The polysaccharide of this invention shows a remarkable increase of viscosity in a diluent solution as described in FIG. 10. This property is specific to this polysaccharide. Further, the diluent solution has a thixotropic property.

The novel polysaccharide of this invention can be utilized in various fields by taking into consideration its specific properties, for example, in food manufacturing as a thickener, tacking reagent, gelling agent, vehicle, tissue restoring reagent, coagulant for suspended particles such as a protein, gelling reagent, anti-syneresis reagent, stabilizing reagent for emulsification, meat binder, perfume-retentive reagent, etc.; in the medical field as a vehicle, anti-tumor reagent, artificial viscera, stabilizing reagent for emulsification, etc.; in the agricultural field as a soil-reforming agent, manure granulating reagent, diet component for domestic animals, component of sericultural feed, pasting reagent for fertilizer, etc.; in other industrial fields as a sizing agent, flocculant, gelling agent for explosives, fire fighting component, paste, component of water-soluble paints, abrasive, etc.

One advantage of this invention is that the fermentation material, especially the carbon source, can be selected with regard to the use mode of the polysaccharide.

Typical examples of this invention are shown below.

EXAMPLE 1

[Arthrobacter carbazolum] *The microorganism* (FERM-2574, ATCC-31258) was inoculated with platinum loop in a 500 milliliter Sakaguchi flask containing ethanol (1.56%), carbazole (1%), $K_2HPO_4$ (0.2%), $MgSO_4.7H_2O$ (0.025%) and $FeSO_4.7H_2O$ (0.001%) on a tap water (pH:8.0), and the cultivation was carried out for 4 days at 30° C. by reciprocal shaking.

After the cultivation, an amount of hot water (60° C.) corresponding to nine times the amount of the cultured broth was added to the cultured broth, and cells were removed by centrifugation (10,000 r.p.m., 30 minutes). One third amount (by volume) of cetyl trimethyl ammonium bromide (2% solution) was added to the supernatant with stirring to precipitate a polysaccharide. The polysaccharide precipitated was filtered, and washed twice with 90% ethanol saturated with sodium chloride. Subsequently, one fourth amount (by volume) of water based on the amount of the cultured broth was added to swell, and then washed with five times amount of acetone. After drying, crude polysaccharide (4 grams per liter) was obtained. After dissolving the crude polysaccharide in water (0.1% concentration), cations were removed by using Amberlite IR-120 B, and then one third amount (by volume) of a mixture of chloroform and iso-amylalcohol (4:1) was added. After mixing thoroughly, a supernatant was obtained by centrifugation. The supernatant obtained was dialyzed for 3 days at low temperature in water. After dialysis, vacuum drying was applied and thus purified polysaccharide (3.6 grams per liter) was obtained.

EXAMPLE 2

An experiment was carried out in the same manner as in Example 1, except that carbazole, one of the fermentation sources, was replaced by 0.8% of peptone. As a result, 1.8 grams per liter of polysaccharide were obtained.

EXAMPLE 3

The same experiment as described in Example 1 was carried out, except that carbazole was replaced by 0.2% of potassium nitrate, 0.01% of corn steep liquor was also added, and the cultivation period was 48 hours. As a result, 1.5 grams per liter of crude polysaccharide were obtained.

EXAMPLE 4

The same experiment as described in Example 1 was carried out, except that ethanol and carbazole were replaced by 4% of starch and 0.8% of peptone. As a result, crude and purified polysaccharide were obtained with yields of 4.2 grams per liter and 3.6 grams per liter, respectively.

EXAMPLE 5

An experiment was carried out in the same manner as in Example 3, except that 1.0% of disodium/hydrogen phosphate hydrated with 12 $H_2O$ and 0.55% of potassium dihydrogen phosphate were used in place of dipotassium/hydrogen phosphate, and 0.2% of ammonium nitrate was used in place of potassium nitrate. As a result, crude and purified polysaccharide were obtained with yields of 6.0 grams per liter and 5.0 grams per liter, respectively.

What is claimed is:

1. A process of producing a polysaccharide having a gel forming property which is characterized by the following properties: (1) comprising (a) glucose, (b) mannose, (c) dihydrostreptose and (d) 3-O-(1' carboxyethyl)-L-rhamnose, the molar ratio of said constituents being (a):(b):(c):(d)=10:10:1-3:3-8, and (2) containing an O-acetyl group in an amount of from 8 to 14 weight percent calculated as acetic acid;

which comprises cultivating [a] *the* microorganism [Arthrobacter carbazolum] *strain FERM 2574 (ATCC-31258) or a polysaccharide producing mutant thereof* in a medium containing assimilable carbon sources and nitrogen sources until said polysaccharide is formed and substantially accumulated in the culture, and recovering the accumulated polysaccharide therefrom.

[2. Process according to claim 1, wherein the microorganism is the strain of Arthrobacter carbazolum FERM 2574 (ATCC-31258) or a polysaccharide producing mutant thereof.]

* * * * *